United States Patent [19]

Eberly, Jr.

[11] 4,358,297
[45] Nov. 9, 1982

[54] REMOVAL OF SULFUR FROM PROCESS STREAMS

[75] Inventor: Paul E. Eberly, Jr., Baton Rouge, La.

[73] Assignee: Exxon Research and Engineering Company, Florham Park, N.J.

[21] Appl. No.: 222,054

[22] Filed: Jan. 2, 1981

Related U.S. Application Data

[63] Continuation-in-part of Ser. No. 109,144, Jan. 2, 1980, abandoned.

[51] Int. Cl.³ .............................................. B01D 53/04
[52] U.S. Cl. ........................................... 55/62; 55/73; 55/75; 423/230
[58] Field of Search .................... 55/62, 73, 75, 33; 252/455 Z, 463; 423/230

[56] References Cited

U.S. PATENT DOCUMENTS

| | | | |
|---|---|---|---|
| 2,882,243 | 4/1959 | Milton | 55/75 X |
| 3,024,868 | 3/1962 | Milton | 55/73 X |
| 3,070,639 | 12/1962 | Geerts et al. | 252/463 X |
| 3,078,634 | 2/1963 | Milton | 55/73 X |
| 3,078,640 | 2/1963 | Milton | 55/73 |
| 3,078,641 | 2/1963 | Milton | 55/73 |
| 3,085,380 | 4/1963 | Dillman et al. | 55/73 X |
| 3,087,291 | 4/1963 | Jackson et al. | 55/73 X |
| 3,300,324 | 1/1967 | Fails | 55/73 X |
| 3,492,083 | 1/1970 | Lowicki et al. | 55/73 X |
| 3,816,975 | 6/1974 | Collins | 55/33 |
| 4,028,069 | 6/1977 | Nolley, Jr. et al. | 55/73 X |

FOREIGN PATENT DOCUMENTS 871076 6/1961 United Kingdom .

OTHER PUBLICATIONS

Petroleum Refiner, vol. 36, No. 7, pp. 136-140, Jul. 1957, Examine These Ways to Use Selective Adsorption.
Linde Molecular Sieves Brochure: Dry Gas, 1957, 19 pp.
Breck, Zeolite Molecular Sieves, 1974, pp. 537-540.

*Primary Examiner*—Robert H. Spitzer
*Attorney, Agent, or Firm*—Llewellyn A. Proctor

[57] ABSTRACT

A process wherein a particulate sorbent mass of zeolite which has been ion-exchanged with zinc or cadmium to provide pore size openings of about 5Å, and greater, particularly zinc, is contacted with a moist hydrocarbon process stream which contains sulfur, sulfur compounds, and other contaminants, these being adsorbed onto said particulate sorbent mass, and the process stream thereby denuded of said sulfur, sulfur compounds, and other contaminants. Thereafter, the sulfur, sulfur compounds, and other contaminants, are readily desorbed, or removed from said particulate sorbent mass by contacting, and purging same with a gas stream, suitably hydrogen, or a hydrogen-containing gas, at elevated temperature.

9 Claims, No Drawings

REMOVAL OF SULFUR FROM PROCESS STREAMS

BACKGROUND OF THE INVENTION AND PRIOR ART

This is a Continuation-in-Part of application Ser. No. 109,144, filed Jan. 2, 1980, now abandoned.

Sulfur occurs in many industrial processes, and sulfur, or sulfur containing compounds, for varying reasons must often be removed from process streams, e.g., flue gas, waste gas or recycle gas streams. This has been accomplished, e.g., by contacting the sulfur-containing process stream with a sorbent comprising a particulate oxide, hydrated oxide, or hydroxide of alumina, zinc, iron, nickel, cobalt or the like, alone or in admixture with each other or with additional materials, e.g., alkali or alkaline earth metal oxides or the like. Reference is made, e.g., to U.S. Pat. No. 3,492,083 and British Pat. No. 871,076 (1957) which describes processes of this type. Hot spherical pebbles have also been used to remove sulfur from process streams, as described, e.g., in U.S. Pat. No. 2,551,905.

The quality of these sorbents for the removal of sulfur varies considerably, and in many applications it is necessary to scrub essentially all of the sulfur from the process streams. This is done for process reasons, as well as environmental reasons. Sulfur, for example, is a well known catalyst poison which finds its way into a process principally via the feed, and it can gradually accumulate upon and poison a catalyst. Essentially all petroleum feeds contain sulfur. Most of the sulfur, because of this adverse effect, is generally removed from the feed, e.g., by contact with nickel or cobalt oxide guard chambers.

Catalytic reforming, a hydroforming, a well-known and important process employed in the petroleum refining industry for improving the octane quality of naphthas and straight run gasolines, is illustrative of a process where the presence of sulfur can have a detrimental effect. Sulfur unavoidably enters the process, principally as a part of the feed. In a typical reforming process, a series of reactors are provided with fixed beds of sulfided platinum-containing catalysts which are sequentially contacted with a naphtha feed, and hydrogen, and each reactor is provided with a preheater, or interstage heater, because the reactions which take place are endothermic. $C_5+$ hydrocarbons as a product is taken from the last reactor of the series, and a hydrogen-sulfide contaminated hydrogen gas stream is separated therefrom and recycled to the several reactors of the series.

In use of the more recently developed multi-metallic platinum catalysts wherein an additional metal, or metals hydrogenation-dehydrogenation component is added as a promoter to the platinum, it has become essential to reduce the feed sulfur to only a few parts, per million parts by weight of feed (ppm), because of the sulfur sensitiveness of these catalysts. For example, in the use of platinum-rhenium catalysts it is generally necessary to reduce the sulfur concentration of the feed well below about 10 ppm, and preferably well below about 2 ppm, to avoid excessive loss of catalyst activity and $C_5+$ liquid yield.

The sulfur must also be scrubbed from the hydrogen recycle gas stream because this too is a source of catalyst sulfur contamination. The vapor effluent from the last reactor of the series is thus a gas rich in hydrogen, which generally contains hydrogen chloride and chlorine, as well as hydrogen sulfide, moisture and small amounts of normally gaseous and $C_5$-$C_9$ hydrocarbons. It is essential to separate hydrogen from the $C_5+$ liquid product and recycle it to the process; and it is essential to remove the sulfur from the moist recycle hydrogen gas stream. This, as suggested, has been accomplished by the use of guard chambers filled with metal oxides, e.g., zinc oxide, supra.

Zinc oxide thus has been used as a sorbent for selectively removing hydrogen sulfide from process streams. Usually, the zinc oxide is contacted with the gas at elevated temperatures to scrub out the sulfur. Such sorbent, however, has not proven successful because the adsorption rate is too low, and it has not been possible to regenerate such sorbent in a reducing atmosphere such as hydrogen due to the high thermodynamic stability of zinc sulfide. Regeneration of this material requires oxidation of the sulfur, or sulfur-containing compounds, so that the sulfur is evolved as sulfur oxides, an environmentally unacceptable product. Such regeneration impairs the mechanical strength of the material. Moreover, sulfur oxides are difficult to remove from flue gas effluents, e.g., as contrasted with hydrogen sulfide which is easily scrubbed from the stream with a caustic or amine solution.

Wolf and co-workers studied the adsorption of hydrogen sulfide and methyl mercaptan on exchanged synthetic sodium—A zeolites as a function of the degree of cation exchange. F. Wolf, W. Hoese & H. Fuertig (Martin-Luther Univ. Halle-Wittenberg; Chemiekombinat Bitterfeld VEB) *Chem. Tech.* (Leipz.) 27 #6:362-64 (June 1975). For hydrogen sulfide, the capacities were found to decrease in the order barium < potassium < strontium < cobalt < nickel < zinc < manganese < sodium < magnesium < calcium. For methyl mercaptan the capacities were found comparable. The capacities of sodium X and sodium-potassium X sieves for both sulfur compounds were slightly higher than those of the corresponding A sieves. In earlier work some members of the same group has found that zinc-A was relatively poor in adsorbing mercaptans. F. Wolf & K. H. Bergk (Univ. Hauc) *Erdoel Kohle, Erdgas, Petrochem Brennst. -Chem.* 27 #10:629 (Oct. 1974); and this work was later confirmed by Soviet researchers E. I. Shcherbina, V. A. Yakubovich & L. I. Mikhalrkaya (Beloruss. Technol. Inst., Minsk) *Neflekhimya* 17 #1:151-55 (Jan.-Feb. 1977).

German Pat. No. 2,226,531 which issued June 1973 to Gebr Herrmann discloses that Pb zeolites can be used for hydrogen sulfide sorption, and that the lead can be exchanged by other metals, inclusive of zinc. The Patentee, however, states that such exchanged zeolites have not been found of practical use.

Robert M. Milton's U.S. Pat. Nos. 3,078,640 and 3,024,868, which issued on applications filed in the last weeks of the year 1959, are believed to exemplify the state-of-the-art as relates to the separation of sulfur-containing compounds from gaseous mixtures by the use of molecular sieve adsorbents. In U.S. Pat. No. 3,078,640, which issued Feb. 26, 1963, certain forms of zeolite A are suggested for use in the selective adsorption of hydrogen sulfide from a vapor mixture containing at least one member of the group consisting of hydrogen, carbon dioxide and normal saturated aliphatic hydrocarbons containing less than nine carbon atoms per molecule. The reference suggests that zeolite A can be used in its sodium form, or the sodium ions of the zeolite can be substituted at least in part by other metal ions from Group I and Group II of the Period Table. The reference states that the various ion exchanged forms of zeolite A includes the lithium, ammonium, silver, zinc, nickel hydrogen and strontium forms. It is stressed that the divalent metal substituted forms of zeolite A, e.g., zinc, nickel and strontium zeolite A, behave quite differently from the monovalent metal substituted forms of zeolite A, e.g., lithium, and hydrogen zeolite A. It suggests that any cationic form of zeolite A having a pore size of at least 4 Angstroms is suitable for practicing the invention; and conversely that smaller pore size forms are unsatisfactory because they do not admit hydrogen sulfide and mercaptans. Albeit, however, this reference describes the use of molecular sieves having pore sizes greater than 4 Å as a selective adsorbent for the separation of sulfur-containing compounds from hydrocarbons, there is no suggestion of the separation, or adsorption, of sulfur containing compounds from moisture bearing, or water containing streams. The separation of sulfur compounds from moist, or wet streams presents a far more difficult problem inasmuch as water is preferentially adsorbed to the exclusion of sulfur containing compounds, and e.g., water generally replaces essentially all of the hydrogen sulfide from an adsorbent contacted with a stream containing both water and hydrogen sulfide.

On the other hand, in U.S. Pat. No. 3,024,868, which issued Mar. 13, 1962, there is specifically described a process useful for the separation of sulfur containing compounds from moist vaporous streams. In particular, the process described is one useful for removing moisture and sulfur containing compounds, notably hydrogen sulfide, from the recycle hydrogen gas stream of a reformer by contact of the stream with crystalline zeolitic molecular sieves having pore sizes ranging from about 3.6 to 4 Å. Both the water and sulfur containing compounds are sorbed preferentially, to the exclusion of the saturated paraffinic hydrocarbons. It is expressly stated that molecular sieves having larger pore sizes, viz. >4 Å, strongly preferentially adsorb and concentrate the $C_4$ and higher paraffins. Any substitution of the sodium zeolite A with monovalent or divalent metal ions which enlarges the pore size beyond this limit is thus, according to Milton, to be avoided. This adverse effect, according to Milton, is particularly apparent with divalent cation forms of zeolite, the enlargement being manifested above about 25 percent substitution of divalent ions in the molecular sieve structure. Data presented in the patent show that zeolite 4 A has eight to ten times the adsorptive capacity for water and hydrogen sulfide as zeolite 5 A and zeolite 13 X, with concurrent high exclusion or rejection of the hydrocarbons.

In Milton's process a reformer recycle hydrogen gas stream is desulfided by contact with at least two separate beds of the zeolite 4 A, the wet reformer hydrogen gas stream being contacted with a first bed in an adsorption stroke at relatively low temperature and pressure, while water and sulfur containing compounds are desorbed from a second bed in a desorption stroke at relatively high temperature and pressure. The flows between the beds are periodically reversed such that the first bed is on an adsorption stroke while the second bed is on a desorption stroke, and vice-versa.

Whereas commercial processes based on the use of metal oxides for adsorption of sulfur from process streams have provided varying degress of success, there is little evidence that the zeolites have attracted any significant commercial interest, if any, for this use. A considerable need therefore exists for the development of new and improved processes of this type, especially those which are capable of adsorbing, and separating sulfur containing compounds from moist hydrocarbon streams; notably hydrogen sulfide-containing reforming hydrogen recycle gas.

It is, accordingly, the primary object of the present invention to fill this need.

A specific object is to provide a new and improved process, particularly one utilizing a sorbent which is capable of high rates of sulfur adsorption from process streams, and more particularly one which can be regenerated without significant loss of mechanical strength, if any.

A more specific object is to provide a process as characterized which utilizes a sorbent which readily adsorbs hydrogen sulfide from gas streams, a sorbent which can be regenerated by simply stripping the hydrogen sulfide from the sorbent with a gas, and the hydrogen sulfide readily removed from the stripping gas, suitably by contact with an alkali or amine solution.

A yet more particular object is to provide a process which utilizes a somewhat admirably suitable for selectively removing hydrogen sulfide, and other sulfur compounds and contaminants at high effectiveness from a recycle hydrogen stream, particularly a moisture bearing acidic recycle hydrogen stream as employed in a reforming operation, especially one which permits recovery of the adsorbed hydrogen sulfide, as hydrogen sulfide, from the sorbent by use of a simple gas purge.

These objects and others are achieved in accordance with the present invention, embodying a process wherein a particulate sorbent mass of zeolite which has been ion-exchanged with zinc or cadmium, particularly zinc, sufficient to provide pore size openings greater than 4 Å, preferably 5 Å and greater, most preferably from about 5 Å to about 13 Å, is contacted with a moisture bearing, hydrocarbon process stream which contains sulfur, sulfur compounds, and other contaminants, these are adsorbed onto said particulate mass of ion-exchanged zeolite, and the process stream thereby denuded of said sulfur, sulfur compounds, and other contaminants. Thereafter, the sulfur, sulfur compounds, and other contaminants, are readily desorbed, or removed from said particulate mass of ion-exchanged zeolite by contacting, and purging same with a gas stream, suitably hydrogen, hydrogen-containing gas, or inert gas such as nitrogen or methane at elevated temperature.

Various zeolites ion-exchanged with zinc or cadmium metals are useful in accordance with this invention inclusive of intermediate and large pore zeolites. Preferred ion-exchange zeolites include mordenite, faujasite, erionite, ferrierite, zeolite A, ZSM-5, zeolite X and Y, chabazite, both natural and synthetic having pore size openings greater than 4 Å, preferably 5 Å and greater; especially those having pore size openings ranging from about 5 Å to 13 Å. The A type zeolite is preferred, especially one which is ion-exchanged with a zinc salt, sufficient to provide pore size openings of about 5 Å, and greater. Exchange of at least about 25 percent, and certainly 65 percent of the sodium ions of an A type zeolite with zinc, or cadmium, is found to produce zeolite 5 A. In fact, it is found that the adsorption behavior of most of the zeolites, especially zeolite A, begins to change when greater than about 25 percent of the sodium ions are exchanged with the multivalent cation, zinc or cadmium, the pore size openings increasing their normal sizes, especially zeolite A which increases beyond 4 Å. Such divalent forms of zeolite A are found far more effective for the selective adsorption of sulfur containing compounds than the small pore species of zeolite A previously known for such use, supra.

In a preferred operation, a particulate mass of ion-exchanged zeolite, notably zinc exchanged zeolite, is charged, or packed into a guard chamber, of series of guard chambers. More preferably, the series of zinc exchanged zeolite guard chambers are employed in parallel, this permitting active use of one guard chamber, or set of serially aligned guard chambers for contact, and purification of a process stream while the other guard chamber, or set of serially aligned guard chambers, is cut out of series for regeneration. In the treatment of a hydrogen recycle gas stream, as employed in reforming, it is found that the hydrogen sulfide can be readily adsorbed from the stream despite the high moisture content of the gas. This is mildly surprising because it is well known that the selectivity of many sorbents for hydrogen sulfide is adversely affected in the presence of water. As a class, the zeolites, in particular, show a preferential adsorption for water, this resulting in a low capacity of the zeolites for the selective removal of hydrogen sulfide. The zinc, and cadmium-exchanged zeolite, notably the zinc exchanged zeolite, shows a high capacity for adsorption of the hydrogen sulfide, several times that of many sulfur sorbent materials. No special preparation of the particulate ion-exchanged zeolite of this invention is required, and it can be employed in a guard chamber as powder, spheres, tablets, pellets, extrudates, irregular shaped particles, or the like in virtually any size.

The temperature of contact is not critical, and there is no necessity to heat or cool the process stream, notably the recycle gas stream. Suitably, the recycle hydrogen stream is contacted with the particulate zinc exchanged zeolite sorbent at normal gas stream temperatures, i.e., at temperatures ranging from about ambient to about 500° F., or more generally at temperatures ranging from about 100° F. to about 300° F.

It would appear, surprisingly, that the metal atoms of the zeolite structure, notably the zinc atoms of the zinc exchanged zeolite, forms simple adsorption bonds with the sulfur compound, this being sufficient to remove, e.g., hydrogen sulfide from a recycle hydrogen gas stream. Unlike the mechanism involved in the removal of a sulfur compound, e.g., hydrogen sulfide, from a recycle hydrogen gas stream by the use of zinc oxide, there is no chemical reaction wherein zinc sulfide is formed. Apparently, as a consequence thereof the zinc exchanged zeolite is readily regenerated by simply purging, or sweeping the sulfur compound therefrom with a hot, non-reactive, or inert gas after it has become sufficiently saturated with the sulfur compound. In the preferred practice of this invention, the zinc exchanged zeolite is simply contacted, purged, or swept with a hydrogen gas stream at elevated temperature to remove the hydrogen sulfide, and other sulfur compounds, and thereby regenerate the zinc exchanged zeolite. Suitably, the purge is conducted by maintaining the hydrogen gas at temperatures ranging from about 300° F. to about 1200° F., preferably from about 500° F. to about 1000° F. Since burning in the presence of oxygen as practiced in the regeneration of many sorbents is unnecessary, the hydrogen sulfide is recovered as hydrogen sulfide rather than as sulfur oxides. Consequently, the hydrogen gas stream itself is readily cleansed of the hydrogen sulfide by washing the gas with a caustic or amine solution.

The invention will be more fully understood by reference to the following examples, and comparative data which demonstrate the high selectivities for hydrogen sulfide of the zeolites of this invention in the presence of water. All terms are given in weight units except as otherwise specified.

EXAMPLES

A series of different commercially known zeolites, as identified hereafter, were exchanged with an aqueous solution of zinc chloride, $ZnCl_2$. This was followed by filtration and washing until the filtrate was free of chloride as determined by testing with a $AgNO_3$ solution. The zeolites were then vacuum dried, and calcined in air for three hours at 800° F. To measure $H_2S$ adsorption, the zeolite was packed into a quartz reactor maintained at 200° F. and a stream of 2000 ppm. $H_2S$ in $H_2$ at atmospheric pressure passed through until breakthrough occured. This was observed by the discoloration of lead acetate paper. For regeneration, the adsorbents were heated either to 500° F. or to 932° F. while stripping with $H_2$ gas. The adsorption of $H_2S$ was then redetermined at a standardized temperature of 200° F. Data on several Zn exchanged zeolites are shown in the Table and/or compared with the unexchanged or corresponding natural zeolite.

TABLE

Exchanged Zeolites
Wt. % S Adsorbed @ 200° F., 1 Atm.
From A 2000 ppm $H_2S$ In $H_2$ Stream

| Adsorbent | Wt. % Zn | % Na Exchanged | Cycle 1 Original | Cycle 2 After $H_2$ Strip @ 932° F. | Cycle 3 After $H_2$ Strip @ 500° F. |
|---|---|---|---|---|---|
| Na Zeolite A (4A Sieve) | 0 | 0 | 0.22 | — | — |
| Zn Zeolite A (Zn 5A) | 14.5 | 65 | 2.37 | 3.02 | 2.0 |
| Cd Zeolite A | — | 50 | 2.38 | 1.27 | — |
| Ni Zeolite A[a] | — | 16 | 0.76 | 0.58 | — |
| Co Zeolite A | — | 42 | 0.85 | 1.40 | — |
| Cu Zeolite A[a,b] | — | 77 | 0.47 | 0.04 | — |
| Hg Zeolite A[a,b] | — | 100 | 0.40 | — | — |
| Zn Exchanged Erionite | 5.79 | | 1.12 | — | — |
| Natural Chabazite | 0 | 0 | 0.96 | — | — |
| Zn Chabazite | 6.33 | — | 1.51 | 1.87 | — |
| Na Mordenite | 0 | 0 | 1.08 | — | — |
| Zn Mordenite | 3.67 | — | 1.25 | — | — |

[a] Partial destruction of the zeolite A crystal structure occurred during the ion-exchange.
[b] Assuming +2 valence state for Cu and Hg.

From these data, it will be initially observed that the original sodium zeolite A (4 A sieve) had very limited capacity for $H_2S$ under these conditions. The Zn 5 A form, however, had a capacity nearly ten times as great. Furthermore, a simple hydrogen strip was effective for regeneration of the sorbent. The increase in capacity in going from 2.37 wt. % in Cycle 1 to 3.02 wt. % in Cycle 2 is attributable to the higher 932° F. regeneration temperature compared to the 800° F. original air calcination. The regeneration at 500° F. is effective in restoring capacity in Cycle 3 to nearly that observed in Cycle 1.

The sodium form of zeolite A has the formula $Na_{12}[(AlO_2)_{12}(SiO_2)_{12}] \cdot XH_2O$, this material being designed 4 A because 4 Å approximates the effective pore size openings of this material in Angstroms. Zeolite 4 A will not adsorb propane. When zeolite A is ion-exchanged with potassium so that its chemical composition becomes $K_{12}[(AlO_2)_{12}(SiO_2)_{12}] \cdot XH_2O$, its effective diameter becomes 3 A and hence is known as 3A. It adsorbs $H_2O$, $NH_3$, and methanol but not ethane.

If zeolite A is exchanged with sufficient of a multivalent cation, e.g., Ca, the effective pore diameter can become 5 Å, and such material is designated as 5 A. This material will adsorb n-paraffins such as n-heptane. It is well known, e.g., by reference to the literature that at least 25% of the Na ions have to be exchanged with calcium to enables its pore diameter to increase in size (See, e.g., U.S. Pat. No. 3,024,968, col. 3, lines 36–44). Profound changes in adsorption behavior also occur when greater than 25% of the sodium ions are exchanged with a multivalent cation, e.g., Ca. In accordance with the present invention the various forms of zeolite are ion-exchanged with zinc or cadmium, preferably zinc; and where the pore openings of the zeolite are of lesser effective diameter than 5 Å the zeolite is nonetheless suitable if the diameters of the pore size opening can be increased by exchange to provide pore openings of about 5 Å, and greater. Of course, zeolite with pore size diameters initially greater than 5 Å effective pore size diameter need only be ion-exchanged with zinc or cadmium, preferably zinc, to render them suitable for use in accordance with the present invention.

With continued reference to the Table, it will be observed that zinc exchanged with chabazite improves its capacity, and the material can also be regenerated by hydrogen. Although the capacity is generally less than that of Zn4 A, chabazite is structurally more stable in acid environments. The other acid resistant zeolites, mordenite and erionite, also show improved capacity for $H_2S$ adsorption upon Zn exchange.

A feature of this invention lies in the improved selectivity of the ion-exchanged zeolites of this invention for $H_2S$ removal from reformer recycle gas. This permits the realization or higher activity, of yields and stability for reforming catalysts, notably bimetallic catalysts. Unlike ZnO, the Zn zeolites also serve to remove water and to be easily regenerable with hydrogen stripping.

It is apparent that various modifications and changes can be made without departing from the spirit and scope of the invention.

For example, the ion-exchanged molecular sieves of this invention can be used in combination with metal alumina spinels as disclosed in U.S. Ser. No. 109,159, filed Jan. 2, 1980, U.S. Pat. No. 4,263,020, e.g., by charging each type of adsorbent to guard chambers and using the guard chambers in series. The ion-exchanged molecular sieves show good sulfur adsorption properties, and superior water adsorption properties. The metal alumina spinels show superior sulfur adsorption properties.

Having described the invention, what is claimed is:

1. A process for the removal of sulfur from a moisture-bearing, sulfur containing hydrocarbon process stream which comprises contacting said stream with a particulate mass of zeolite sufficiently ion-exchanged with cadmium to provide pore size openings of about 5 Å, and greater, to adsorb sulfur thereon, and after completion of the sulfur sorption cycle, contacting said ion-exchanged zeolite with an essentially non-reactive gas or reducing gas at elevated temperature, the sulfur being desorbed and the sorbent thereby regenerated.

2. The process of claim 1 wherein the gas employed to desorb the sulfur from the ion-exchanged zeolite is comprised of hydrogen.

3. The process of claim 1 wherein the cadmium exchanged zeolite sorbent is contacted with an essentially hydrogen gas at elevated temperature to desorb the sulfur and regenerate the sorbent.

4. The process of claim 3 wherein the hydrogen is contacted with said cadmium exchanged zeolite sorbent at temperatures ranging from about 400° F. to about 1200° F.

5. The process of claim 4 wherein the hydrogen is contacted with said cadmium exchanged zeolite sorbent at temperatures ranging from about 800° F. to about 1000° F.

6. A process for the removal of sulfur from a moisture-bearing, sulfur containing process stream wherein a series of on-stream reactors are provided with beds of a sulfur sensitive platinum-containing catalyst, a naphtha feed with hydrogen is cocurrently passed sequentially through said series of reactors, and a vaporous effluent rich in hydrogen is taken from the last reactor of the series, hydrogen is separated from the products and recycled, the improvement which comprises contacting said stream with a particulate mass of zeolite sufficiently ion-exchanged with cadmium to provide pore size openings of about 5 Å, and greater, to adsorb sulfur thereon, and after completion of the sulfur sorption cycle, contacting said ion-exchanged zeolite with an essentially non-reactive gas or reducing gas at elevated temperature, the sulfur being desorbed and the sorbent thereby regenerated.

7. The process of claim 6 wherein the cadmium exchanged zeolite sorbent is contacted with an essentially hydrogen gas at elevated temperatures to desorb the sulfur and regenerate the sorbent.

8. The process of claim 7 wherein the hydrogen is contacted with said cadmium exchanged zeolite sorbent at temperatures ranging from about 400° F. to about 1200° F.

9. The process of claim 8 wherein the hydrogen is contacted with said cadmium exchanged zeolite sorbent at temperatures ranging from about 800° F. to about 1000° F.

* * * * *